United States Patent [19]

Thöne

[11] Patent Number: 4,466,275
[45] Date of Patent: Aug. 21, 1984

[54] ARRANGEMENT FOR MEASURING VISCOSITY

[76] Inventor: Ernst Thöne, Hamburg, Fed. Rep. of Germany

[21] Appl. No.: 326,475

[22] Filed: Dec. 2, 1981

[51] Int. Cl.³ .............................................. G01N 11/12
[52] U.S. Cl. ...................................................... 73/57
[58] Field of Search .................... 73/57; 364/509, 550, 364/556

[56] References Cited

U.S. PATENT DOCUMENTS

| | | | |
|---|---|---|---|
| 2,672,047 | 3/1954 | Spear | 73/57 |
| 3,368,391 | 2/1968 | Harrison et al. | 73/57 |
| 3,772,910 | 11/1973 | McGinn et al. | 73/57 |
| 4,027,516 | 6/1977 | Ochodnicky et al. | 73/57 |
| 4,048,020 | 9/1977 | Romovacek | 73/57 |

FOREIGN PATENT DOCUMENTS 2912628  10/1980  Fed. Rep. of Germany .......... 73/57

Primary Examiner—James J. Gill
Attorney, Agent, or Firm—Peter K. Kontler

[57] ABSTRACT

An arrangment for measuring the viscosity of a fluid includes a heated, vertical container which receives a vessel filled with the fluid to undergo a viscosity determination. A pair of vertically spaced sensors are mounted in the peripheral wall of the container and are connected with an evaluating mechanism which includes a timer and a computer. The sensors are also connected with a temperature regulating mechanism which regulates the temperature of the fluid by controlling heating of the container. In operation, the fluid is heated on a predetermined temperature. A standard sphere is then permitted to fall through the fluid. When the sphere passes the uppermost sensor, the latter generates an impulse which activates the timer. Similarly, an impulse deactivating the timer is generated when the sphere passes the lowermost sensor. The time required for the sphere to travel between the sensors is fed into the computer which then calculates the viscosity of the fluid from a relationship between viscosity and time. The calculated viscosity may be displayed on a digital indicator. The arrangement is simple to operate and eliminates the need for manual observations to determine the time required for the standard sphere to travel a predetermined distance through the fluid.

25 Claims, 3 Drawing Figures

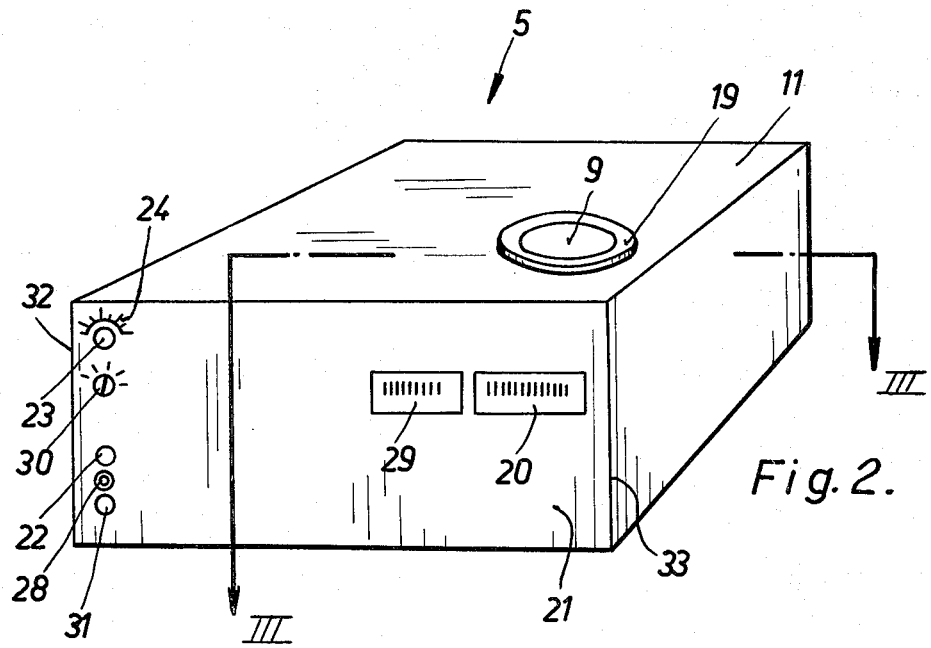
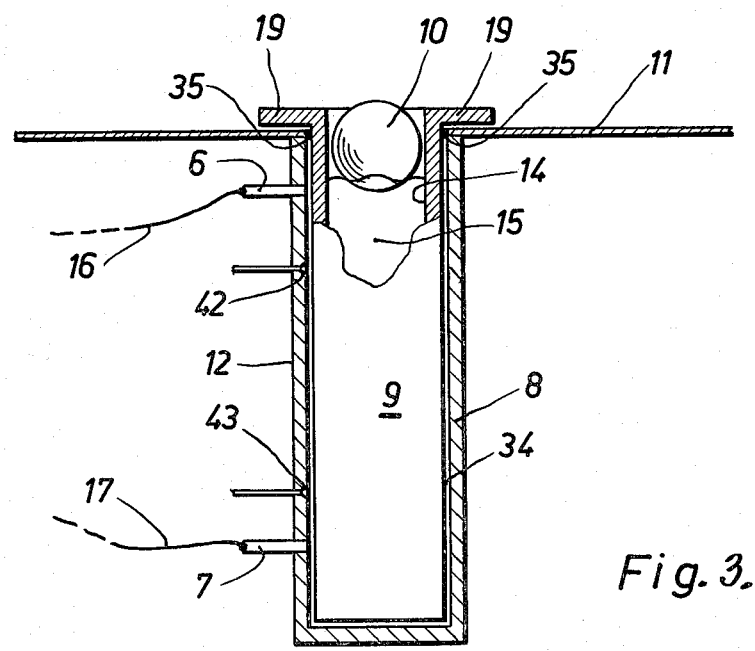

ARRANGEMENT FOR MEASURING VISCOSITY

BACKGROUND OF THE INVENTION

The invention relates to an arrangement for measuring the viscosity of a fluid.

More particularly, the invention relates to an arrangement for measuring the viscosity of a fluid by determining the time required for a standard element to travel a predetermined distance through the fluid.

Viscosity measurements are performed with either a discharge or falling ball viscometer. In the discharge viscometer, the time required for a predetermined quantity of the fluid to flow through an opening of predetermined cross section is measured. In the falling ball viscometer, on the other hand, the time required for a standard element, e.g. a sphere, of known weight and dimensions to fall a predetermined distance through a column of the fluid is measured. The viscosity in each case is a function of the elapsed time which is normally measured with a stop watch.

It has been found that precise time measurements cannot be obtained with conventional viscometers. Accordingly, the viscosity cannot be determined with the desired accuracy. This is especially true for viscometers which are intended to be transportable.

The falling ball viscometer is particularly prone to inaccuracies. These inaccuracies stem from parallax. Thus, the falling ball viscometer has a transparent vessel which accommodates the fluid and is engraved with marks which respectively indicate the beginning and end of the zone along which the standard element is timed. Parallax makes it difficult to determine the precise instant at which the standard element passes a mark. The errors due to parallax are particularly large in the frequent cases where viscosity measurements are performed on murky fluids such as, for example, used motor oil, lubricating oil and fuel. Here, the murkiness of the fluid affects the precision of the timing to such a degree that a well-defined viscosity cannot be obtained and the viscosity can be determined only to within a predetermined scatter range.

Furthermore, the known viscometers are primarily designed for use at a fixed location and are difficult to transport. However, there are situations where it is desirable to have a truly portable viscometer. For instance, it is highly desirable to rapidly measure the viscosity of fuel oil at the point of delivery.

Moreover, the determination of viscosity with conventional viscometers is inconvenient in that it requires the use of tables which relate the viscosity to the time required for the standard element to travel a predetermined distance through the fluid. Aside from the inconvenience, significant errors in addition to those arising from parallax may occur from inaccuracies in the tables.

OBJECTS AND SUMMARY OF THE INVENTION

It is an object of the invention to provide an arrangement of the falling ball type which enables viscosity to be measured with a high degree of precision.

Another object of the invention is to provide an arrangement of the falling ball type which enables viscosity to be determined without the use of tables.

An additional object of the invention is to provide an arrangement of the falling ball type which is truly portable.

A concomitant object of the invention is to provide an arrangement of the falling ball type which enables viscosity measurements to be performed at a substantially constant temperature.

The preceding objects, and others which will become apparent as the description proceeds, are achieved by the invention.

The invention resides in the provision of an arrangement for measuring the viscosity of a fluid which comprises a vessel for accommodating a body of the fluid, and sensing means for generating impulses in response to movement of a standard element, e.g. a sphere, through a predetermined zone of the vessel. Evaluating means is provided for determining the travel time of the standard element through the predetermined zone from the impulses generated by the sensing means.

One embodiment of the arrangement further includes temperature regulating means for controlling the temperature of the body of fluid.

In a preferred embodiment of the arrangement, the sensing means, evaluating means and temperature regulating means are combined as a unit in a box or receptacle.

The arrangement of the invention renders it possible to simply and precisely determine the time required for the standard element to travel a predetermined distance through the fluid. This is achieved by making the determination of the travel time independent of manual observations. An automatic determination of the travel time is obtained via impulses generated when the standard element passes by the sensing means which is preferably located outside of the fluid. The impulses automatically initiate and terminate timing of the standard element so that manual observations are no longer necessary. This eliminates the main source of errors, namely, parallax, found in conventional viscometers. Furthermore, by designing the evaluating means appropriately, the travel time of the standard element may be converted into viscosity. In this manner, the viscosity of the fluid may be obtained as soon as the measurement of the travel time has been completed and without reference to tables. It is thus possible to immediately compare the actual viscosity with a reference viscosity thereby enabling automatic control functions to be performed.

The arrangement in accordance with the invention has the advantage that all of the devices required for precision viscosity measurements are combined into a single unit. The arrangement is thus easy to handle and maintain and makes it possible for viscosity measurements to be performed even by unskilled labor.

The novel features which are considered as characteristic of the invention are set forth in particular in the appended claims. The improved arrangement itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 2 is a perspective view of the arrangement of FIG. 1; and

FIG. 3 is a partly cross-sectional view in the plane indicated by the arrows III—III of FIG. 2.

DESCRIPTION OF THE PREFERRED EMBODIMENTS

Figure 1:
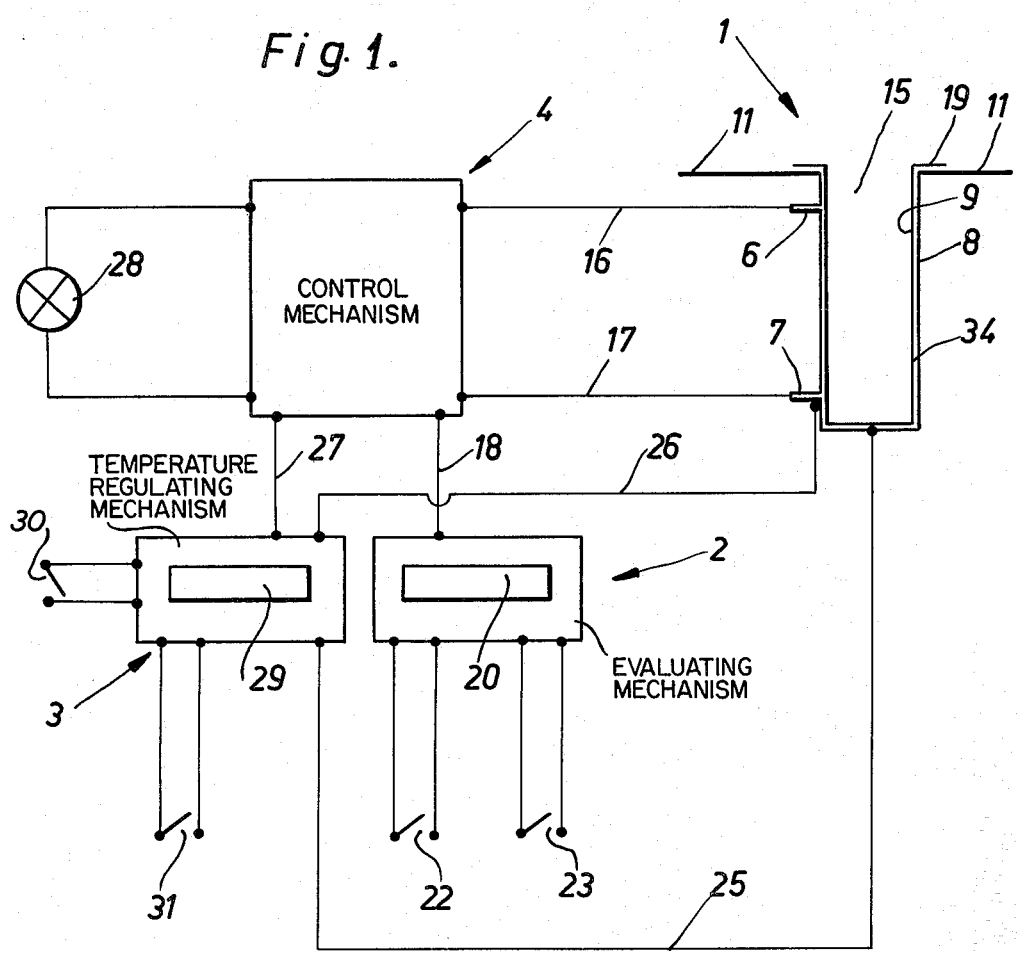
FIG. 1 diagrammatically illustrates an arrangement in accordance with the invention for measuring viscosity.

FIG. 1 illustrates the components of an arrangement according to the invention for measuring viscosity. The arrangement includes a sensing mechanism 1, an evaluating mechanism 2, a temperature regulating mechanism 3 and a control mechanism 4. The evaluating mechanism 2 and the temperature regulating mechanism 3 are connected with the sensing mechanism 1 via the control mechanism 4. The sensing mechanism 1, evaluating mechanism 2, temperature regulating mechanism 3 and control mechanism 4 are combined as a unit in a box or receptacle 5 as shown in FIG. 2.

Referring to FIGS. 1 and 3, the sensing mechanism 1 includes a container 8 and a pair of sensors 6 and 7 which are mounted in a peripheral wall 12 of the container 8. The container 8 is secured to the box 5 and is accommodated within the latter in its entirety. The container 8 is vertically oriented and has an open upper end in the region of an upper wall 11 of the box 5.

The sensor 6 is located directly above the sensor 7, that is, the sensors 6 and 7 are located on a vertical line. The sensors 6 and 7 are capable of emitting sensing signals and are positioned in such a manner that the sensing signals travel into the interior of the container 8 along superimposed horizontal paths. The sensor 6 marks the beginning of a predetermined vertical measuring zone within the container 8 while the sensor 7 marks the end of this zone.

The container 8 receives a vessel 9 which accommodates a column 15 of the fluid to undergo a viscosity determination. The vessel 9 is located almost entirely within the container 8. The inner dimensions of the container 8 and the outer dimensions of the vessel 9 are selected in such a manner that a narrow gap 34 exists between the container 8 and the vessel 9. The upper end of the gap 34 is closed by a seal 35 which is arranged between the vessel 9 and the upper wall 11 of the box 5.

The vessel 9 has an open upper end which is provided with a rim 19. The rim 19 covers the seal 35 and rests on the upper wall 11 of the box 5 thereby supporting the vessel 9. The vessel 9 is composed of a material, e.g. V₄A, which can be penetrated by the signals generated by the sensors 6 and 7. The thickness of the peripheral wall 14 of the vessel 9 is so selected in dependence upon the material of the vessel 9 that the signals from the sensors 6 and 7 can travel into the fluid column 15.

The sensor 6 is connected with the control mechanism 4 via a conductor 16 while the sensor 7 is connected with the control mechanism 4 via a conductor 17. A conductor 18 leads from the control mechanism 4 to the evaluating mechanism 2. The latter is constituted by a timer, a computer and a digital indicator 20. The timer is arranged to be activated in response to an impulse generated by the sensor 6 and to be deactivated in response to an impulse generated by the sensor 7. The timer is advantageously in the form of a device such as, for example, a frequency modulator, which generates time-dependent signals, that is, which generates signals in a number proportional to the elapsed time. Such signals may be counted by the evaluating mechanism 2 and the number of signals generated between activation and deactivation of the timer is then an indicator of the elapsed time.

In order to perform a viscosity measurement, the vessel 9 is filled with the fluid which is to undergo a viscosity determination and is placed in the container 8. Care should be taken in filling the vessel 9 to insure that the fluid does not overflow when a standard element, that is, an element of known weight and dimensions, is placed in the vessel 9. The standard element is here in the form of a sphere 10 as illustrated in FIG. 3.

Once the filled vessel 9 has been inserted in the container 8, the sphere 10 is placed in the vessel 9 and permitted to fall through the column 15 of the fluid. When the sphere 10 reaches the level of the sensor 6, and accordingly the level of the signal track generated by the sensor 6, the latter generates an impulse. This impulse is transmitted to the control mechanism 4 via the conductor 16. The control mechanism 4 then activates the timer of the evaluating mechanism 2 via the conductor 18 so that the timer begins timing as soon as the sphere 10 passes through the signal track of the sensor 6. When the sphere 10 reaches the level of the sensor 7, and thus the level of the signal track generated by the sensor 7, the latter sends an impulse to the control mechanism 4 via the conductor 17. The control mechanism 4 then shuts off the timer of the evaluating mechanism 2.

The elapsed time between activation and deactivation of the timer, which is the time required for the sphere 10 to travel through the measuring zone between the sensors 6 and 7, is fed into the computer of the evaluating mechanism 2. The computer calculates the viscosity of the fluid by multiplying the elapsed time with appropriate parameters which have been preprogrammed into the computer. The multiplications are performed in accordance with an equation relating the viscosity to the time required for the sphere 10 to travel through the measuring zone between the sensors 6 and 7. The evaluating mechanism 2 can thus display the viscosity directly and it is to this end that the evaluating mechanism 2 is provided with the digital indicator 20. The viscosity can be read directly from the digital indicator 20 without any further calculations immediately after measurement of the time required for the sphere 10 to travel through the measuring zone between the sensors 6 and 7. As illustrated in FIG. 2, the digital indicator 20 is mounted on a front wall or panel 21 of the box 5 which is normal to the upper wall 11 of the box 5.

A clearing switch 22 is arranged on the front wall 21 of the box 5. With reference to FIG. 1, the clearing switch 22 is connected with the digital indicator 20. The clearing switch 22 serves to clear the digital indicator 20 before the next measurement is begun so that the digital indicator 20 is free to display a new viscosity. The computer of the evaluating mechanism 2 may have a memory and be interconnected with the digital indicator 20 and the switch 22 in such a manner that the viscosity displayed on the digital indicator 20 is stored in the memory when it is cleared by the switch 22. It then becomes possible to run a series of repeat viscosity measurement and obtained an arithmetic average of these measurements after the series has been completed. The arithmetic average may again be displayed on the digital indicator 20.

Referring still to FIG. 1, a switch 23 is connected with the computer and functions to program the computer with the specific gravity of the fluid to undergo a viscosity measurement. This enables the arrangement of the invention to be used for measuring the viscosities of fluids having different specific gravities. As shown in FIG. 2, the switch 23 is advantageously in the form of a selector switch which is circumscribed by a scale 24 marked with different specific gravities. The computer can then be programmed for any specific gravity by simply setting the switch 23 to the appropriate value on the scale 24. The switch 23 makes it possible to successively measure the viscosities of fluids having different specific gravities.

In order to obtain comparable results, viscosity measurements on a fluid must be performed at a specific temperature. To this end, the arrangement of the invention includes the temperature regulating mechanism 3 which heats the fluid column 15 in the vessel 9 via the container 8 and maintains the temperature of the fluid column 15 constant during the measurement period.

The container 8 is designed to be heated and is provided with a heating element for this purpose. The heating element is arranged to direct heat only towards the interior of the container 8. As seen in FIG. 3, temperature sensing elements 42 and 43 are mounted in the peripheral wall 12 of the container 8 and the tips of the temperature sensing elements 42 and 43 project into the gap 34 between the container 8 and the vessel 9.

With reference to FIG. 1, the temperature regulating mechanism 3 is connected with the heating element in the container 8 via a conductor 25 and with the temperature sensing elements 42 and 43 via a conductor 26. The temperature sensing elements 42 and 43 transmit signals indicative of the temperature of the fluid column 15 to the temperature regulating mechanism 3 via the conductor 26.

The temperature regulating mechanism 3 is also connected with the control mechanism 4 via a conductor 27. When the temperature sensing elements 42 and 43 indicate that the fluid column 15 has reached the required temperature, the temperature regulating mechanism 3 sends an impulse to the control mechanism 4 via the conductor 27. The control mechanism 4, in turn, activates the sensors 6 and 7. A lamp 28 connected with the control mechanism 4 lights up when the sensors 6 and 7 are activated. This signifies that the arrangement is ready for operation.

The temperature regulating mechanism 3 may be provided with a digital indicator 29 for displaying the temperature of the fluid column 15. A selector switch 30 for selecting the temperature of the fluid column 15 is connected with the temperature regulating mechanism 3. In addition, the temperature regulating mechanism 3 is provided with an on-off switch 31 which activates and deactivates the temperature regulating mechanism 3 and thereby the entire arrangement.

In order to simplify handling and maintenance, the lamp 28, the temperature selector switch 30, the on-off switch 31 and the digital temperature indicator 29 are arranged on the front wall 21 of the box 5 together with the digital viscosity indicator 20, the clearing switch 22 and the specific gravity selector switch 23 as shown in FIG. 2. The switches 22, 23, 30 and 31, as well as the lamp 28, are located on a vertical line adjacent a vertical edge 32 of the front wall 21. The digital indicators 20 and 29, on the other hand, are disposed horizontally next to one another in the region of the opposite vertical edge 33 of the front wall 21.

To regulate the temperature of the fluid column 15, the temperature selector switch 30 is set to the temperature which is prescribed for measuring the viscosity of the particular fluid in the vessel 9. The temperature regulating mechanism 3 then activates the heating element in the container 8 via the conductor 25. The temperature of the fluid column 15 is sensed by the temperature sensing elements 42 and 43 which project into the gap 34 between the container 8 and the vessel 9 and is displayed on the digital indicator 29. The temperature sensing elements 42 and 43 transmit signals indicative of the temperature to the temperature regulating mechanism 3 via the conductor 26. When the temperature selected by means of the temperature selector switch 30 is attained, the temperature regulating mechanism 3 sends an impulse to the control mechanism 4 which then activates the sensors 6 and 7. The lamp 28 lights up indicating that the arrangement is ready for operation.

The presence of the gap 34 between the container 8 and the vessel 9 is advantageous for temperature regulation of the fluid column 15. The heat which emanates from the container 8 heats the air in the gap 34 and the heated air then flows uniformly about the vessel 9 thereby uniformly heating the fluid column 15 therein. The temperature sensing elements 42 and 43 monitor the fluid temperature and enable a predetermined temperature to be achieved and maintained during the measurement period. The seal 35, as well as the rim 19 of the vessel 9, prevent escape of the heated air from the gap 34.

To perform a viscosity measurement, the filled vessel 9 is placed in the container 8 and the specific gravity selector switch 23 is rotated to the specific gravity of the fluid. The measurement temperature is set by means of the temperature selector switch 30 and the arrangement is then switched on via the on-off switch 31. This initiates heating of the container 8, and the temperature rise of the fluid can be followed on the digital indicator 29. When the measurement temperature is reached, the lamp 28 lights up thereby indicating that the arrangement is ready for operation. The sphere 10 can now be inserted into the vessel 9. The viscosity calculated from the travel time of the sphere 10 through the measuring zone between the sensors 6 and 7 is displayed on the digital indicator 20.

If a series of measurements is to be performed, the sphere 10 is removed from the vessel 9 after the first measurement has been completed. This may, for example, be accomplished with a bar magnet. Before repeating the measurement, the viscosity displayed on the digital indicator 20 is cleared by the clearing switch 22 and stored in the memory of the evaluating mechanism 2 thereby freeing the digital indicator 20 to display the result of the next viscosity measurement. After completion of the series of measurements, the viscosities stored in the memory may be averaged and the average viscosity displayed on the digital indicator 20.

The design of the vessel 9 permits it to be readily removed from the container 8 once the viscosity measurements have been completed and to be easily cleaned.

The specific gravity of the fluid and the measurement temperature may be programmed into the arrangement via a single switch rather than by two individual switches 23 and 30 as illustrated. This may, for instance, be accomplished by replacing the switches 23 and 30 with a single fluid selector switch, that is, a switch which can be set to a particular type of fluid, e.g. a specific type of oil. The specific gravity and temperature scales are then replaced by a single scale indicating various types of fluids. By appropriately setting the fluid selector switch, both the specific gravity and measurement temperature corresponding to the selected fluid are automatically programmed into the arrangement.

It is further possible to design the evaluating mechanism 2 so that a reference viscosity for the type of fluid selected is displayed on the digital indicator 20 in addition to the measured viscosity. This enables the reference and actual viscosities to be compared during performance of the viscosity measurements so that deviations of the actual viscosities from the reference viscosity may be determined immediately.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. An arrangement for measuring the viscosity of a fluid by measuring the time which elapses during travel of a standard element through a predetermined distance in such fluid, comprising a vessel for accommodating a body of the fluid whose viscosity is to be measured; a container accomodating said vessel and defining therewith a narrow gap; sensing means including a pair of sensing devices installed in said container at said predetermined distance from one another, said sensing means being arranged to generate impulses in response to movement of the standard element past said sensing devices; temperature regulating means including at least one temperature sensing device installed in said gap for monitoring the temperature of the fluid in said vessel and heating means for heating such fluid; control means connected to both the sensing means and the temperature regulating means, said control means being arranged to regulate the temperature of the fluid in said vessel and to actuate the sensing means when the temperature of the fluid in said vessel reaches a desired value; and evaluating means connected to said sensing means for measuring the travel time of the standard element through said predetermined distance from the impulses generated by said sensing means and for calculating the viscosity of the fluid based on said travel time, said evaluating means being programmable relative to specific gravity and temperature.

2. An arrangement as defined in claim 1, wherein said sensing, evaluating and temperature regulating means are combined as a unit.

3. An arrangement as defined in claim 2, further comprising a receptacle for said unit.

4. An arrangement as defined in claim 3, wherein said container is a part of said sensing means and is fixed to said receptacle.

5. An arrangement as defined in claim 4, wherein said sensing devices are located on a substantially vertical line and are positioned to transmit sensing signals towards said vessel.

6. An arrangement as defined in claim 4, wherein said receptacle has an upper wall and said container is disposed in the interior of said receptacle substantially in its entirety and has an open end in the region of said upper wall.

7. An arrangement as defined in claim 6, wherein said container is substantially vertical and said open end is the upper end of said container.

8. An arrangement as defined in claim 6, wherein said gap extends to said upper wall of said receptacle and said vessel has a rim which supports said vessel on said upper wall and covers said gap.

9. An arrangement as defined in claim 1, further comprising an on-off switch for activating and deactivating said heating means.

10. An arrangement as defined in claim 1, wherein said heating means is arranged to radiate heat only towards said gap.

11. An arrangement as defined in claim 1, wherein said temperature regulating means further comprises indicating means for indicating the temperature of the body of fluid.

12. An arrangement as defined in claim 11, wherein said indicating means comprises a digital indicator.

13. An arrangement as defined in claim 1, further comprising a selector switch for selecting the temperature of the body of fluid.

14. An arrangement as defined in claim 1, wherein said evaluating means comprises signal-generating means for generating time-dependent signals, computing means for calculating the viscosity of a fluid from the time-dependent signals, and indicating means for indicating the viscosity calculated by said computing means.

15. An arrangement as defined in claim 14, further comprising a selector switch for programming said computing means with the specific gravity of the fluid.

16. An arrangement as defined in claim 14, wherein said indicating means comprises a digital indicator.

17. An arrangement as defined in claim 16, wherein said sensing means is arranged to activate said signal-generating means when the standard element reaches one of said sensing devices and to deactivate said signal-generating means when the standard element advances beyond the other of said sensing devices, said computing means being programmed to convert the number of time-dependent signals generated by said signal-generating means during passage of the standard element between said sensing devices into information which is directly indicative of viscosity of the fluid in said vessel.

18. An arrangement as defined in claim 16, further comprising a clearing switch for clearing said digital indicator.

19. An arrangement as defined in claim 18, wherein said computing means has a memory and said computing means, digital indicator and clearing switch are interconnected in such a manner that a viscosity displayed by said digital indicator is stored in said memory upon clearing of said digital indicator by said clearing switch, said computing means being adapted to average the viscosities stored in said memory and thereby obtain an average value for a series of viscosity measurements performed on the fluid, said digital indicator being arranged to display the thus-obtained average value.

20. An arrangement as defined in claim 1, further comprising means for indicating that said sensing means is activated.

21. An arrangement as defined in claim 20, wherein said indicating means comprises a lamp.

22. An arrangement as defined in claim 1, wherein said evaluating means comprises computing means for calculating the viscosity of the fluid from the travel time of the standard element between said sensing devices.

23. An arrangement as defined in claim 1, wherein said vessel is substantially vertical.

24. An arrangement as defined in claim 1, wherein said sensing means is located externally of said vessel and the material and wall thickness of said vessel are selected in such a manner as to permit sensing signals generated by said sensing means to travel to the interior of said vessel.

25. An arrangement for measuring the viscosity of a fluid comprising:

(a) a vessel for accomodating a body of the fluid; and (b) a unit accommodated in a receptacle and including sensing means for generating impulses in response to movement of a standard element through a predetermined zone of said vessel, evaluating means for determining the travel time of the standard element through said zone from the impulses generated by said sensing means, and temperature regulating means for controlling the temperature of the body of fluid wherein said evaluating means include computing means for calculating the viscosity of the fluid and a first digital indicator for indicating the calculated viscosity, said temperature regulating means including a second digital indicator for indicating the temperature of the body of fluid; and further comprising control means for activating and deactivating said sensing means, a lamp for indicating that said sensing means is activated, heating means for heating the body of fluid in said vessel, an on-off switch for activating and deactivating said heating means, a clearing switch for clearing said first digital indicator, a first selector switch for programming said computing means with the specific gravity of the fluid, and a second selector switch for selecting the temperature of the body of fluid, said digital indicators, switches and lamp being arranged on a front panel of said receptacle.

* * * * *